(12) United States Patent
Kinney

(10) Patent No.: US 6,548,248 B1
(45) Date of Patent: Apr. 15, 2003

(54) DNA STERILIZATION INDICATOR

(75) Inventor: Dennis Kinney, Queens, NY (US)

(73) Assignee: Propper Manufacturing Co., Inc., Long Island City, NY (US)

( * ) Notice: Subject to any disclaimer, the term of this patent is extended or adjusted under 35 U.S.C. 154(b) by 0 days.

(21) Appl. No.: 09/437,462

(22) Filed: Nov. 10, 1999

(51) Int. Cl.⁷ .............................................. C12Q 1/68
(52) U.S. Cl. .............................. 435/6; 435/31; 422/26; 422/28
(58) Field of Search ..................... 422/26, 28, 944; 435/6, 31

(56) References Cited

U.S. PATENT DOCUMENTS

| | | | | |
|---|---|---|---|---|
| 5,306,615 A | * | 4/1994 | Breillatt, Jr. et al. | 435/6 |
| 5,604,096 A | * | 2/1997 | Shaeffer et al. | 435/6 |
| 5,648,227 A | * | 7/1997 | Baseboll | 435/7.32 |
| 5,714,166 A | * | 2/1998 | Tomalia et al. | 424/486 |
| 5,770,393 A | | 6/1998 | Dalmasso et al. | 435/31 |
| 5,792,614 A | * | 8/1998 | Western et al. | 435/6 |
| 5,922,592 A | * | 7/1999 | Tautvydas | 435/287.4 |

FOREIGN PATENT DOCUMENTS

| | | | |
|---|---|---|---|
| EP | 0460323 | | 12/1991 |
| EP | 1099764 A2 | * | 5/2001 |

OTHER PUBLICATIONS

L. Panasci et al., "The Effect of Prolonged Incubations and Heat Denaturation on Melphalan–Induced DNA Cross–Links as Measured by the Ethidium Bromide Fluorescence Assay," Cancer Letters 50:129–132 (1990).

* cited by examiner

*Primary Examiner*—Robert J. Warden, Sr.
*Assistant Examiner*—Sean E. Conley
(74) *Attorney, Agent, or Firm*—Ostrolenk, Faber, Gerb & Soffen, LLP

(57) ABSTRACT

A method of determining the effectiveness of a sterilization cycle in a sterilization chamber by the use of an indicator containing DNA and a dye which can be bound thereto. The indicator containing DNA is placed in the sterilization chamber prior to the beginning of the sterilization cycle. When the DNA is subjected to heat and steam, the molecule is fragmented so that it is no longer capable of binding the dye. The DNA is withdrawn from the indicator after the sterilization cycle, contacted by a solution of the dye and, thereafter, dipped into wash water. If sufficient fragmentation has taken place, a substantial percentage of the dye will be washed off during the second dip. This is easily recognized by the operator and the efficacy of the cycle can be determined. On the other hand, if insufficient heat and steam has been applied, the remaining DNA will retain the dye and little or no change in color will be observed. In such a case, the operator will immediately recognize that the sterilization cycle was ineffective.

18 Claims, No Drawings

DNA STERILIZATION INDICATOR

The present Invention is directed to an improved sterilization indicator, particularly one inserted into the sterilization chamber and based upon the interaction between DNA and dyes.

BACKGROUND OF THE INVENTION

Both hospitals and doctors' offices customarily require the presence of devices for sterilization of various medical instruments. These sterilizers are of two basic types, i.e. prevacuum and gravity. In the former case, air is evacuated from the sterilization chamber before the sterilization cycle is initiated. This assists the steam generated in penetrating both the sterilization indicator and the instruments being treated. The gravity cycle is similar to the prevacuum cycle except that no vacuum is applied. The former is almost universally used in hospitals and the latter in doctors' offices and small clinics. Overall, approximately 25% of all sterilizers are of the gravity type, while the remaining are prevacuum. Since the gravity type is smaller and more compact, establishments such as individual doctors' offices and small clinics tend toward their use. The prevacuum type is larger and cumbersome, and is capable of being operated as both a prevacuum sterilizer and a gravity sterilizer. Therefore, it is of importance that any sterilization indication method be suitable for both types of sterilizers.

SUMMARY OF THE INVENTION

The method of determining the effectiveness of the sterilization cycle includes placing the sterilization indicator in the sterilization chamber prior to beginning the sterilization cycle. The indicator contains a DNA preparation consisting of 0.25 to 1.0 $\mu$g of initial DNA per $\mu$l of water. A preferred concentration is 0.25 to 0.50 $\mu$g of initial DNA per $\mu$l. After the sterilization cycle has been completed, the cycled DNA is withdrawn from the sterilization chamber and placed on a support. Preferably, the support is a plastic having a negative surface potential, especially nylon or a nitrocellulose membrane. The latter two have a particular affinity for the DNA. The dye solution is placed on the cycled DNA and thereafter dipped into water and any change in color is observed.

The DNA has the ability to bind dyes within its structure, provided that the molecules are whole and complete. However, when the DNA is subjected to a combination of heat and steam (heat alone is insufficient), the structure breaks down so that the binding is less efficient. Thus, if sufficient heat and steam has contacted the DNA during the sterilization cycle, it will be fragmented and will not retain the dye. Therefore, when the membrane (for example) is dipped into the dye solution and then into water, a substantial and easily observable portion of the dye is dissolved. What remains on the paper looks substantially different from the original.

On the other hand, if the sterilization cycle is not complete, then the DNA molecule is substantially intact. As a result, the dye remains bound and very little will be washed off when it is dipped. Thus, the person carrying out the test can easily determine whether the cycle has done its job properly. Moreover, the results of the test are immediate; there is no need to wait for days or even hours to determine whether a given sterilization cycle has been suitably effective.

The DNA used is high molecular weight double stranded DNA. Obtaining the DNA from salmon sperm is the most economical way of providing this substance, but the source is not critical.

As to the dyes, ethidium bromide is the most tightly bound, followed by methylene blue. The former, however, is carcinogenic and should, therefore, be used only where suitable precautions will be taken. In particular, rubber gloves and similar protective means are suitable precautions to be taken in order to be sure that the dye does not contact the skin. In actual practice, methylene blue is more satisfactory since it is safe. Also, of particular interest are acridine orange and Vistra green, the latter being a product of Amersham Pharmacia Biotech.

The mechanism of binding is not certain. As to ethidium bromide and acridine orange, it is believed that they enter the DNA molecule and are intercalated between the nucleic acid pairs of hydrogen bonds located where the halves of the molecule meet. On the other hand, methylene blue does not intercalate and is less tightly bound to the DNA molecule. As a result, it is easier to wash out when dipped in water.

In some cases, it is desirable to determine the effectiveness of the indicator and this is done by the use of spores of particular microorganisms which are placed therein. Spores of *Bacillus subtilis* and *Bacillus stearothermophilus*, standard test organisms, are quite resistant to heat. At the end of the cycle, the spores of the microorganisms are cultured in the usual way to determine whether there is any growth. No growth indicates that they have been killed and that the sterilization cycle was effective. If the culture grows, then the opposite conclusion is reached. These results are compared with those obtained from the test pack in which the DNA is located, in order to determine that the indicator is operating properly.

In a desirable form of the Invention, the DNA is first subjected to the sterilization cycle. After withdrawal from the autoclave, it is deposited on the membrane (e.g. nitrocellulose or nylon), and a drop of dye solution is deposited thereon. Thereafter, it is dipped into water and observed. If the sterilization cycle is complete, the DNA will have been fragmented and/or the dye will not be bound thereto. Thus, when it is dipped into water, most (or all) of the dye will have been washed off. This is, of course, easily observable by the operator. It has been found particularly useful if some detergent is added to the wash water.

As a preferred form of the Invention, a further sample of the DNA is provided which is not introduced into the sterilization chamber. At the end of the cycle, this is dipped into the dye and then into the wash water and provides a standard for comparing the cycled DNA with the original. This aids in determining whether a change has occurred.

DETAILED DESCRIPTION OF THE INVENTION

In the preferred form of the Invention, DNA in water solution is placed in a vial in the sterilizer. After the cycle is complete, the DNA is withdrawn from the sterilizer and dropped onto a suitable membrane such as nitrocellulose or nylon. This is followed by the application of the dye (e.g. methylene blue) on the DNA. At this point, the DNA is fully colored by the dye. It is then dipped into water and removed. If the sterilization cycle is complete, the DNA will have been fragmented and/or its ability to bind the dye will have been significantly reduced. As a result, most or all of the dye will wash off in the water and the membrane will evidence a substantial lightening of the color.

On the other hand, if the color does not lighten substantially, it indicates that the DNA remains substantially intact so that the dye remains bound to it. This indicates that the sterilization cycle is not complete and appropriate action must be taken. By including a small amount of the detergent in the water, the dye removal will be improved and the test will be more easily read.

The concentration of DNA in the DNA preparation should be 0.25 to 1.0 µg/µl as a practical and realistic range. Above the upper limit, there could be so much DNA present that, even with proper sterilization, there would be enough unbroken molecules to hold the dye so that the difference between the control (no breakdown) and the properly cycled DNA cannot be readily determined. On the other hand, if there is insufficient DNA (below the lower limit), then even an incomplete cycle will cause sufficient breakdown so that the remainder is insufficient to bind enough dye to maintain the color. Thus, outside the foregoing limits, the test becomes less reliable.

EXAMPLE 1

To test the effectiveness of the present Invention in gravity displacement sterilizers, standard DNA preparations (0.25 µg/µl in 300 µl total volume) were subjected to gravity displacement steam sterilization at 250° F. for various periods of time. The DNA containing vials were placed in Propper Bio-Challenge Packs along with Bi-OK Self-Contained Biological Indicators ($D_{250}$=1.8 minutes, $2.0 \times 10^5$ spores per strip). One DNA containing vial and one biological indicator were in each pack and three such packs were used in each run. The results obtained were as follows:

| Exposure Time | DNA Binding Affinity | Spore Growth (# survivors/ # exposed) |
|---|---|---|
| 0 min | ++++ | |
| 18 min | + | 5/6 |
| 30 min | − | 0/6 |

Spore growth was reported after 48 hours growth at 55° C. In the Tables contained herein, each+represents 25% of the binding affinity, "−" indicates zero affinity.

EXAMPLE 2

Standard DNA preparations (0.25 µg/µl in 300 µl total volume) were subjected to prevacuum sterilization at 270° F. for various periods of time. The vials containing the DNA were placed in Propper Bi-OK Steam Packs along with Bi-OK Self Contained Biological Indicators ($D_{250}$=1.8 minutes, $2.0 \times 10^5$ spores per strip). One vial containing DNA and one biological indicator were contained in each pack. Three packs were used for each run and the cycle consisted of four levels of vacuum (−26, −27, −27, and −27 inches of mercury, respectively), applied prior to steam input. The cycles were run for 1 minute, 2 minutes, 3 minutes, and 4 minutes. The following results were obtained.

| Exposure Time | DNA Binding Affinity | Spore Growth (# survivors/# exposed) |
|---|---|---|
| 0 min | ++++ | |
| 1 min | +++ | 5/6 |
| 2 min | ++ | 2/6 |
| 3 min | + | 0/6 |
| 4 min | − to +/− | 0/9 |

Spore growth was reported after 48 hours incubation at 55° C. The symbol "+/−" indicates a maximum of 10% binding affinity remaining.

EXAMPLE 3

Standard DNA preparation (0.25 µg/µl and 0.5 µg/µl in 300 µl total volume) were subjected to 270° F. for various periods of time. The preparation was placed within a Propper Bio-Challenge Pack and the prevacuum cycle consisted of three applications of vacuum (−26, −27, and −27 millimeters of mercury, respectively) drawn prior to steam input. The following binding affinities were noted.

| | DNA Concentration | | Spore Growth |
|---|---|---|---|
| Exposure Time | .25 µg/µl | .5 µg/µl | # Survivors / # Exposed |
| 1 min. | ++ | +++ | 6/6 |
| 2 min. | ++ | +++ | |
| 2.5 min. | + | +++ | 5/6 |
| 4 min. | − | ++ | 0/6 |

As the foregoing Examples amply demonstrate, the DNA indicator in accordance with the present Invention operates reliably for both prevacuum and gravity sterilizers.

Although only a limited number of specific embodiments have been expressly disclosed, the Invention is to be broadly construed and not to be limited except by the character of the claims appended hereto.

I claim:

1. A method of determining the effectiveness of a sterilization cycle, which includes application of heat and steam in a sterilization chamber, said method comprising:

placing a sterilization indicator in said sterilization chamber prior to beginning said sterilization cycle, said sterilization indicator including a DNA preparation containing from 0.25 to 1.0 µg of DNA per µl of water, said DNA being adapted to fragment on being subjected to said sterilization cycle to form fragmented DNA, carrying out said sterilization cycle whereby at least some of said initial DNA is converted into said fragmented DNA, withdrawing said fragmented DNA from said chamber, contacting said fragmented DNA with a dye capable of being bound to said DNA only before fragmentation, dipping said fragmented DNA containing said dye into wash water, and thereafter observing said fragmented DNA.

2. The method of claim 1 wherein said initial DNA is on a support.

3. The method of claim 2 wherein said support is a plastic having a negative surface potential.

4. The method of claim 2 wherein said support is a membrane.

5. The method of claim 4 wherein said membrane is non-porous.

6. The method of claim 4 wherein said support is of nitrocellulose or nylon.

7. The method of claim 1 wherein said DNA is double stranded.

8. The method of claim 1 wherein said second solvent is water.

9. The method of claim 1 wherein said second solvent contains a detergent.

10. The method of claim 1 wherein said sterilization indicator comprises a test micro-organism, culturing said micro-organism after removal from said sterilization chamber whereby the effectiveness of said cycle and said indicator can be determined.

11. The method of claim 10 wherein said micro-organism is selected from the group consisting of *Bacillus subtilis* and *Bacillus stearothemophilus*.

12. The method of claim 1 wherein said dye is selected from the group consisting of ethidium bromide, methylene blue, acridine orange, and Vistra green.

13. The method of claim 12 wherein said dye is methylene blue.

14. The method of claim 2 wherein said support is a porous paper inserted with said DNA.

15. The method of claim 1 wherein said DNA is provided on a substrate which is not introduced into said chamber, dipping said substrate into said solution of said dye and then into said second solvent, thereby acting as a standard of comparison for said fragmented DNA.

16. The method of claim 1 wherein said sterilization cycle is a prevacuum sterilization.

17. The method of claim 1 wherein said sterilization cycle is a gravity sterilization.

18. The method of claim 1 wherein said DNA preparation contains 0.25 to 0.50 $\mu$g of DNA per $\mu$l of water.

* * * * *